US00RE36702E

United States Patent [19]

Green et al.

[11] E Patent Number: Re. 36,702

[45] Reissued Date of Patent: May 16, 2000

[54] SEAL ASSEMBLY FOR ACCOMMODATING INTRODUCTION OF SURGICAL INSTRUMENTS

[75] Inventors: David T. Green, Gulf Stream, Fla.; Salvatore Castro, Seymour, Conn.

[73] Assignee: United States Surgical Corporation, Norwalk, Conn.

[21] Appl. No.: 09/282,473

[22] Filed: Mar. 30, 1999

Related U.S. Patent Documents

Reissue of:

[64] Patent No.: 5,720,759
Issued: Feb. 24, 1998
Appl. No.: 08/589,426
Filed: Jan. 22, 1996

[63] Continuation of application No. 08/317,416, Oct. 3, 1994, abandoned, which is a continuation of application No. 08/091,794, Jul. 14, 1993, abandoned.

[51] Int. Cl.[7] ..... A61B 17/00

[52] U.S. Cl. ..... 606/167

[58] Field of Search ..... 606/167, 185; 604/169, 256, 164

[56] References Cited

U.S. PATENT DOCUMENTS

| | | |
|---|---|---|
| 729,423 | 5/1903 | Scheiber et al. . |
| 2,008,340 | 7/1935 | Salvati et al. . |
| 2,402,306 | 6/1946 | Turkel . |
| 2,797,837 | 7/1957 | Roberts . |
| 3,086,797 | 4/1963 | Webb . |
| 3,197,173 | 7/1965 | Taubenheim . |
| 3,288,137 | 11/1966 | Lund . |
| 3,438,607 | 4/1969 | Williams et al. . |
| 3,487,837 | 1/1970 | Petersen . |
| 3,568,679 | 3/1971 | Reif . |
| 3,683,911 | 8/1972 | McCormick . |
| 3,766,916 | 10/1973 | Moorehead et al. . |
| 3,811,440 | 5/1974 | Moorehead et al. . |
| 3,856,010 | 12/1974 | Moorehead et al. . |
| 3,875,938 | 4/1975 | Mellor . |
| 3,893,446 | 7/1975 | Miller . |
| 3,915,168 | 10/1975 | Monestere et al. . |
| 3,920,215 | 11/1975 | Knauf . |
| 3,970,089 | 7/1976 | Saice . |
| 3,977,008 | 8/1976 | Moorehead . |
| 3,994,287 | 11/1976 | Turp et al. . |
| 4,000,739 | 1/1977 | Stevens . |
| 4,126,133 | 11/1978 | Schwartz . |
| 4,149,535 | 4/1979 | Volder . |
| 4,177,814 | 12/1979 | Knepshield . |
| 4,212,297 | 7/1980 | Johnson, Jr. et al. . |
| 4,231,400 | 11/1980 | Friedling et al. . |
| 4,240,411 | 12/1980 | Hosono . |
| 4,243,034 | 1/1981 | Brandt . |
| 4,318,401 | 3/1982 | Zimmerman . |
| 4,324,239 | 4/1982 | Gordon et al. . |
| 4,378,013 | 3/1983 | LeFevre . |
| 4,380,234 | 4/1983 | Kamen . |
| 4,392,854 | 7/1983 | Ibach . |
| 4,397,641 | 8/1983 | Jacobs . |
| 4,424,833 | 1/1984 | Spector et al. . |
| 4,430,081 | 2/1984 | Timmermans . |
| 4,436,519 | 3/1984 | O'Neill . |

(List continued on next page.)

FOREIGN PATENT DOCUMENTS

| | | |
|---|---|---|
| 0344907 | 12/1989 | European Pat. Off. . |
| 0350291 | 1/1990 | European Pat. Off. . |
| 3042229 | 5/1982 | Germany . |
| 699253 | 11/1953 | United Kingdom . |
| 2019219 | 10/1979 | United Kingdom . |
| 2057269 | 4/1981 | United Kingdom . |
| 2065479 | 7/1981 | United Kingdom . |

*Primary Examiner*—Michael Buiz
*Assistant Examiner*—Vikki Trinh

[57] ABSTRACT

A seal assembly is provided which includes a gimbal-like structure permitting rotation of a mounting member relative to the housing. The rotation of the mounting member allows the seal member to align with an instrument being inserted therethrough. The seal assembly is adapted to be detachably mounted to a cannula assembly for use in endoscopic surgery.

19 Claims, 2 Drawing Sheets

U.S. PATENT DOCUMENTS

| | | |
|---|---|---|
| 4,464,178 | 8/1984 | Dalton . |
| 4,473,369 | 9/1984 | Lueders et al. . |
| 4,475,548 | 10/1984 | Muto . |
| 4,496,348 | 1/1985 | Genese et al. . |
| 4,516,293 | 5/1985 | Beran . |
| 4,519,793 | 5/1985 | Galindo . |
| 4,533,349 | 8/1985 | Bark . |
| 4,579,120 | 4/1986 | MacGregory . |
| 4,580,573 | 4/1986 | Quinn . |
| 4,583,977 | 4/1986 | Shishov et al. . |
| 4,593,681 | 6/1986 | Soni . |
| 4,610,665 | 9/1986 | Matsumoto et al. . |
| 4,610,674 | 9/1986 | Suzuki et al. . |
| 4,626,245 | 12/1986 | Weinstein . |
| 4,632,671 | 12/1986 | Dalton . |
| 4,634,421 | 1/1987 | Hegemann . |
| 4,645,492 | 2/1987 | Weeks . |
| 4,650,474 | 3/1987 | DeBacker . |
| 4,654,030 | 3/1987 | Moll et al. . |
| 4,655,752 | 4/1987 | Honkanen et al. . |
| 4,673,393 | 6/1987 | Suzuki et al. . |
| 4,699,616 | 10/1987 | Nowak et al. . |
| 4,717,385 | 1/1988 | Cameron et al. . |
| 4,723,550 | 2/1988 | Bales et al. . |
| 4,767,411 | 8/1988 | Edmunds . |
| 4,786,028 | 11/1988 | Hammond . |
| 4,798,594 | 1/1989 | Hillstead . |
| 4,817,631 | 4/1989 | Schnepp-Pesch et al. . |
| 4,839,471 | 6/1989 | Clark et al. . |
| 4,842,591 | 6/1989 | Luther . |
| 4,869,717 | 9/1989 | Adair . |
| 4,874,377 | 10/1989 | Newgard et al. . |
| 4,874,378 | 10/1989 | Hillstead . |
| 4,874,380 | 10/1989 | Hesketh . |
| 4,883,053 | 11/1989 | Simon . |
| 4,895,346 | 1/1990 | Steigerwald . |
| 4,895,565 | 1/1990 | Hillstead . |
| 4,897,081 | 1/1990 | Poirier et al. . |
| 4,909,798 | 3/1990 | Fleischhacker et al. . |
| 4,915,694 | 4/1990 | Yamamoto et al. . |
| 4,917,668 | 4/1990 | Haindl . |
| 4,929,235 | 5/1990 | Merry et al. . |
| 4,959,055 | 9/1990 | Hillver . |
| 4,960,259 | 10/1990 | Sunnanvader et al. . |
| 4,960,412 | 10/1990 | Fink . |
| 4,966,589 | 10/1990 | Kaufman . |
| 4,978,341 | 12/1990 | Niederhauser . |
| 5,000,745 | 3/1991 | Guest et al. . |
| 5,009,391 | 4/1991 | Steigerwald . |
| 5,009,643 | 4/1991 | Reich et al. . |
| 5,026,352 | 6/1991 | Anderson . |
| 5,041,095 | 8/1991 | Littrell . |
| 5,053,014 | 10/1991 | Van Heugten . |
| 5,053,016 | 10/1991 | Lander . |
| 5,064,416 | 11/1991 | Newgard et al. . |
| 5,073,169 | 12/1991 | Raiken . |
| 5,104,383 | 4/1992 | Shichman . |
| 5,104,389 | 4/1992 | Deem et al. . |
| 5,127,626 | 7/1992 | Hilal et al. . |
| 5,127,909 | 7/1992 | Shichman . |
| 5,137,520 | 8/1992 | Maxson et al. . |
| 5,158,553 | 10/1992 | Berry et al. . |
| 5,167,636 | 12/1992 | Clement . |
| 5,176,648 | 1/1993 | Holmes et al. . |
| 5,180,373 | 1/1993 | Green et al. . |
| 5,188,609 | 2/1993 | Bayless et al. . |
| 5,197,955 | 3/1993 | Stephens et al. . |
| 5,201,714 | 4/1993 | Gentelia et al. . |
| 5,207,652 | 5/1993 | Kay . |
| 5,209,736 | 5/1993 | Stephens et al. . |
| 5,209,737 | 5/1993 | Ritchart et al. . |
| 5,211,370 | 5/1993 | Powers . |
| 5,215,531 | 6/1993 | Maxson et al. . |
| 5,224,935 | 7/1993 | Hollands . |
| 5,226,891 | 7/1993 | Bushatz et al. . |
| 5,232,453 | 8/1993 | Plass et al. . |
| 5,242,415 | 9/1993 | Kantrowitz et al. . |
| 5,263,939 | 11/1993 | Wortrich . |
| 5,267,968 | 12/1993 | Russo . |
| 5,279,575 | 1/1994 | Sugarbaker . |
| 5,312,364 | 5/1994 | Jacobs . |
| 5,330,436 | 7/1994 | Heidmueller . |
| 5,352,211 | 10/1994 | Merskelly . |
| 5,354,283 | 10/1994 | Bark et al. . |
| 5,356,391 | 10/1994 | Stewart . |
| 5,364,367 | 11/1994 | Banks et al. . |
| 5,366,446 | 11/1994 | Tal et al. . |
| 5,370,625 | 12/1994 | Shichman . |
| 5,375,588 | 12/1994 | Yoon . |
| 5,380,302 | 1/1995 | Orth . |
| 5,391,156 | 2/1995 | Hildwein et al. . |
| 5,395,343 | 3/1995 | Iscovich . |
| 5,830,231 | 11/1998 | Geiges, Jr. ..... 606/205 |

SEAL ASSEMBLY FOR ACCOMMODATING INTRODUCTION OF SURGICAL INSTRUMENTS

Matter enclosed in heavy brackets [ ] appears in the original patent but forms no part of this reissue specification; matter printed in italics indicates the additions made by reissue.

This is a continuation of application Ser. No. 08/317,416, filed on Oct. 3, 1994 which is a continuation of application Ser. No. 08/091,794, filed Jul. 14, 1993, both of which are abandoned.

BACKGROUND OF THE INVENTION

1. Field of the Invention

This invention relates to seal systems which are adapted to allow the introduction of surgical instrumentation into a patient's body. In particular, the invention is applicable to a cannula assembly wherein a cannula housing includes or is adapted to receive a seal assembly to sealingly accommodate instruments of different diameters inserted through the seal assembly and cannula.

2. Description of the Related Art

In laparoscopic procedures surgery is performed in the interior of the abdomen through a small incision; in endoscopic procedures surgery is performed in any hollow viscus of the body through narrow tubes or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly comprised of a cannula assembly and an obturator assembly. Since the cannula assembly provides a direct passage for surgical instrumentation from outside the patient's body to access internal organs and tissue, it is important that the cannula assembly maintain a relatively gas-tight interface between the abdominal cavity and the outside atmosphere. The cannula assembly thus generally includes a cannula attached to a cannula housing containing a seal assembly adapted to maintain a seal across the opening of the cannula housing.

Since surgical procedures in the abdominal cavity of the body require insufflating gases to raise the cavity wall away from vital organs, the procedure is usually initiated by use of a Verres needle through which a gas such as CO2 is introduced into the body cavity, thereby creating a pneumoperitoneum. Thereafter, the pointed obturator of the obturator assembly is inserted into the cannula assembly and used to puncture the abdominal wall. The gas provides a positive pressure which raises the inner body wall away from internal organs, thereby providing the surgeon with a region within which to operate and avoiding unnecessary contact with the organs by the instruments inserted through the cannula assembly. Following removal of the obturator assembly from the cannula assembly, laparoscopic or endoscopic surgical instruments may be inserted through the cannula assembly to perform surgery within the abdominal cavity.

Without the obturator assembly to block the flow of insufflation gas out from the cavity, other structure must be provided to maintain a relatively fluid-tight interface between the abdominal cavity and the outside atmosphere. Generally in the context of insufflatory surgical procedures, there are two sealing requirements for cannula assemblies. The first requirement is to provide a substantially fluid-tight seal when an instrument is not being introduced into or is not already present in the cannula. The second requirement is to provide a substantially fluid-tight seal when an instrument is being introduced into or is already present in the cannula. Additionally, as endoscopic and laparoscopic surgical procedures and techniques have advanced, it has become desirable to accommodate surgical instrumentation of varying outside diameters through a single cannula assembly in a given surgical procedure, thereby minimizing the number of cannulae required and facilitating efficiency in the surgical procedure.

To meet the first sealing requirement, various seals have been provided for maintaining the pneumoperitoneum in the cavity when no trocar or other surgical instrument is present in the cannula. For example, a pivotally mounted flapper valve may be provided which pivots open upon insertion of an instrument and pivots closed, under a spring bias, once the instrument is removed. Conventional flapper valves may also be manually opened by pivoting a lever provided on the exterior of the housing. An example of such a flapper valve is disclosed in U.S. Pat. No. 4,943,280 to Lander. Trumpet valves are also well known for use in sealing a cannula assembly in the absence of a surgical instrument.

U.S. Pat. No. 4,655,752 to Honkanen et al. discloses a cannula including a housing and first and second seal members. The first seal member is conically tapered towards the bottom of the housing and has a circular opening in its center, while the second seal member is cup-shaped. The second seal member includes at least one slit to allow for passage of instruments.

U.S. Pat. No. 4,929,235 to Merry et al. discloses a self-sealing catheter introducer having a sealing mechanism to prevent blood or fluid leakage that includes a planar sealing element having a slit, and a conical sealing element distal of said planar sealing element so that if the distal conical sealing element is moved distally it rests upon the planar sealing element, each sealing element being adapted to surround a tube.

U.S. Pat. Nos. 4,874,377 and 5,064,416 to Newgard et al. relate to a self-occluding intravascular cannula assembly in which an elastomeric valving member is positioned transversely to a housing and is peripherally compressed to cause displacement, distortion and/or rheological flow of the elastomeric material. A frustoconical dilator projection is provided which cooperates with the elastomeric valving member in moving the valving member to a non-occluding position.

U.S. Pat. No. 5,104,3838 to Shichman relates to a trocar adapter seal which is adapted to be associated with a cannula assembly and which advantageously reduces the diameter of the cannula assembly to accommodate instruments of smaller diameter. The trocar adapter seal may be removed from the cannula assembly so that the cannula assembly may once again accommodate instruments of larger diameter. WO 93/04717 to Mueller et al. describes a similar trocar adapter seal system in which a pair of seal adapter plates are slidably mounted to the cannula housing and may be selectively positioned transverse the cannula housing aperture for accommodating surgical instrumentation therethrough.

Cannula assemblies have also been developed which are provided with a series of resilient sealing elements having a central aperture, e.g., commonly assigned, co-pending applications Ser. No. 07/874,291 filed Apr. 24, 1992 and Ser. No. 07/873,416 filed Apr. 24, 1992. Upon insertion of an instrument, the sealing elements resiliently receive the instrument, while maintaining a seal around the instrument across a range of instrument diameters, e.g., 5 to 12 mm. Upon withdrawal of the instrument, a fluid-tight seal is provided by the internal sealing elements.

Although attempts have been made to provide a seal assembly as part of or for use in conjunction with a cannula assembly which maintains the integrity of the seal between the body cavity and the atmosphere outside the patient's body, seal systems provided to date have failed to address the full range of surgeons' needs, especially when it is desired to utilize different instruments having different diameters therethrough.

SUMMARY OF THE INVENTION

The present invention provides a seal assembly which will allow a surgeon to efficaciously utilize instruments of varying diameter in a surgical procedure. The seal assembly of the invention obviates the need for multiple adapters to accommodate instruments of varying diameter by providing an apertured resilient seal member which is mounted in a gimbal-like assembly, thereby facilitating alignment of the instrument with the aperture of the seal member.

In accordance with the present invention, a seal assembly is provided which includes a housing that defines a concave ring-like track on its inner face. The seal assembly further includes a mounting member to which a resilient seal member is mounted. The mounting member has a convexly oriented arcuate outer wall that is configured and dimensioned to ride within the ring-like track. An axial cylindrical guide wall is preferably associated with the mounting member to guide surgical instruments into alignment with the aperture of the seal member. A limiter ring is also preferably associated with the housing to limit the range of motion of the mounting member relative to the housing. In a preferred embodiment, the limiter ring limits the angular motion of the mounting member to between 20 to 25 degrees relative to the axis of the housing. Internal structure may also be provided within the housing to ensure a fluid tight seal distal to the resilient seal member, e.g., a flexible bellows member.

The resilient seal member of the invention is configured and dimensioned to provide a fluid-tight seal with instruments of varying diameter. In one embodiment, the resilient seal member is cone shaped and includes an aperture of approximately 4 mm diameter. The resilience of the material from which the seal member is fabricated, e.g., polyisoprene, allows the aperture to expand or stretch to accommodate instruments of greater diameter, e.g., up to 12 mm in diameter. Structure may also be provided adjacent the proximal side of the conical seal member, e.g., multi-lobed seal protector elements, to protect the resilient seal member from puncture or laceration as a surgical instrument aligns itself with the central aperture.

Preferably, the seal assembly of the invention is adapted to be associated with a cannula assembly. The cannula assembly typically includes a tubular cannula and a cannula housing within which is positioned a cannula seal assembly. The seal cannula assembly typically provides structure which is adapted to provide a fluid-tight seal in the absence of a surgical instrument. Suitable cannula seal assemblies include a spring loaded flapper valve, a trumpet valve, a duck bill valve, or the like. The seal assembly of the invention may be associated with the cannula housing by any suitable means, e.g., a bayonnet lock.

In use, the seal assembly of the invention may be associated with a cannula assembly at any point the surgeon desires flexibility in the instrument sizes he may utilize therethrough. Thus, for example, if the surgeon is utilizing a 12 mm cannula assembly in an endoscopic surgical procedure and determines that it would be advantageous to have the flexibility to use instruments ranging in size from 4 to 12 mm through that cannula assembly, the seal assembly of the invention may be secured to the cannula assembly. Thereafter, instruments ranging in diameter from 4 to 12 mm may be efficaciously introduced therethrough. The cylindrical guide wall guides the instrument toward the aperture of the resilient seal member. The mounting member rides within the ring-like track, angularly repositioning itself with respect to the housing in response to force exerted thereon by the instrument contacting a wall thereof.

The movement of the mounting member relative to the housing which is accommodated by the gimbal-like structure of the present invention also facilitates seal maintenance once an instrument is being used within the body cavity. In particular, as an instrument is manipulated, the resilient seal member transversely repositions itself through movement of the mounting member relative to the housing, thereby ensuring that the resilient seal member maintains a fluid-tight seal around the instrument shaft.

BRIEF DESCRIPTION OF THE DRAWINGS

The foregoing features of the present invention will become more readily apparent and will be better understood by referring to the following detailed description of preferred embodiments of the invention, which are described hereinbelow with reference to the drawings wherein.

DETAILED DESCRIPTION OF THE INVENTION

The present invention contemplates the use of all types of endoscopic and laparoscopic surgical instruments therethrough including, but not limited to, clip appliers, surgical staplers, lasers, endoscopes, laparoscopes, forceps, photographic devices, graspers, dissectors, suturing devices, scissors, and the like. All of such devices are referred to herein as "instruments".

The seal assembly of the present invention, either alone or in combination with a seal system internal to a cannula assembly, provides a substantial seal between a body cavity of a patient and the outside atmosphere before, during and after insertion of an instrument through the cannula assembly. Moreover, the seal assembly of the present invention is capable of accommodating instruments of varying diameters, e.g., from 5 mm to 15 mm, by providing a gas tight seal with each instrument when inserted. The flexibility of the present seal assembly greatly facilitates endoscopic surgery where a variety of instruments having differing diameters are often needed during a single surgical procedure.

Figure 1:
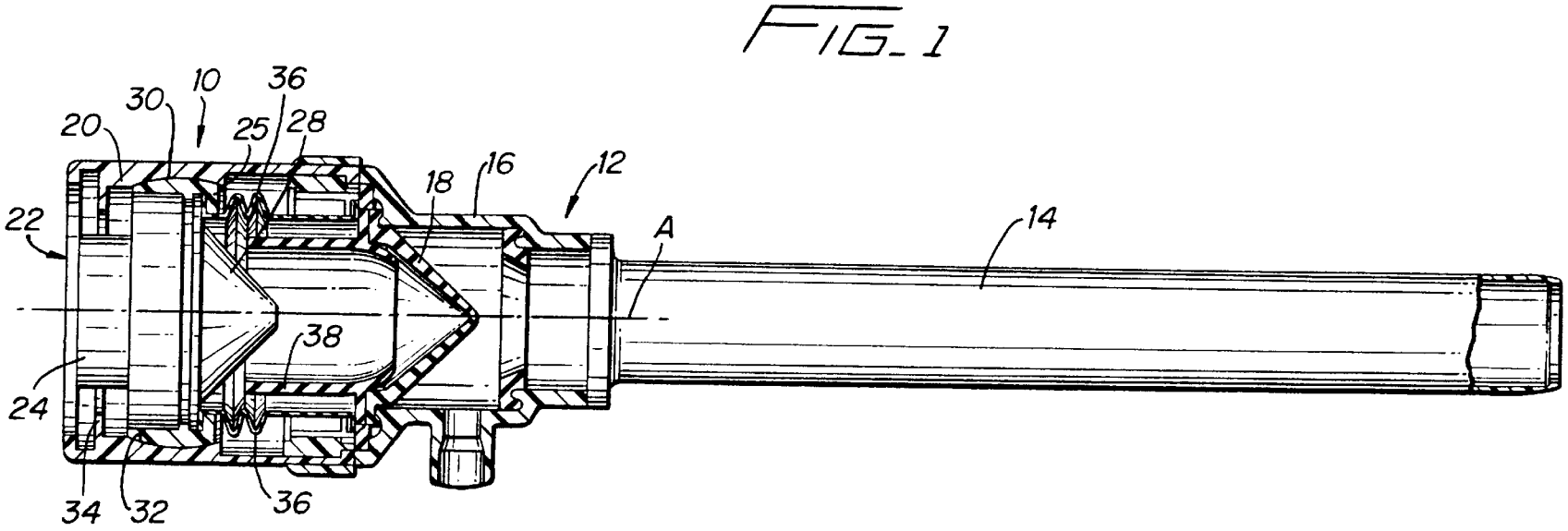
FIG. 1 is a side view, partially in section, of a seal assembly of the present invention mounted to a cannula assembly.
Figure 2:
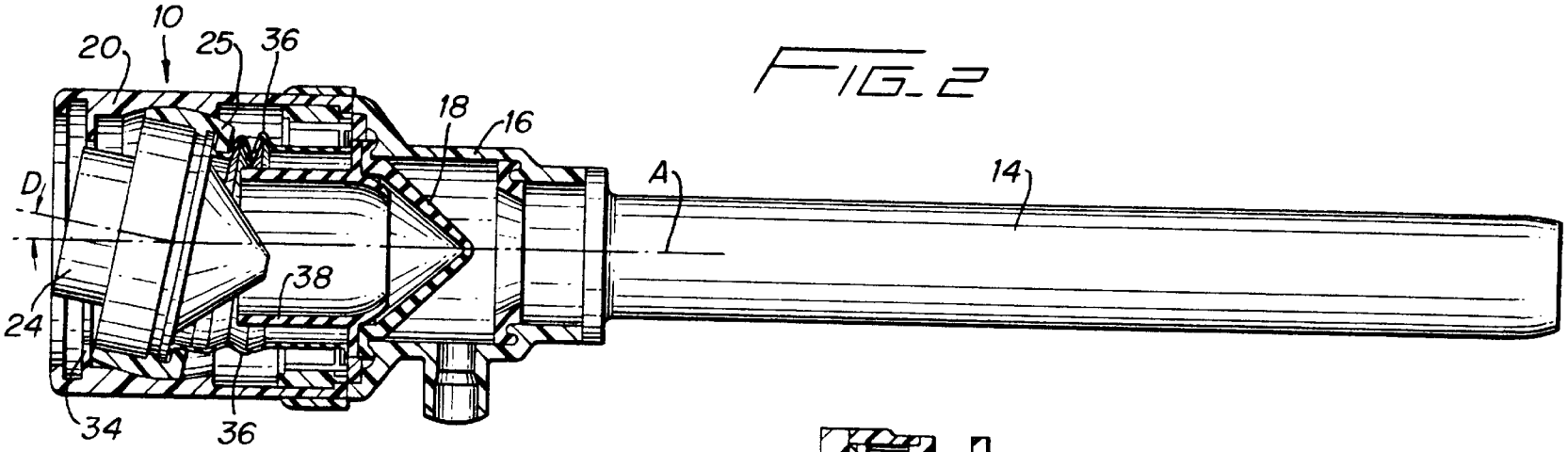
FIG. 2 is a side view of the assembly of FIG. 1 with the mounting member and associated structure in a second position.

Referring to the drawings, in which like reference numerals identify identical or similar parts, FIGS. 1 and 2 illustrate seal assembly 10 mounted to cannula assembly 12. Cannula assembly 12 includes a cannula 14 and a cannula housing 16. Within cannula housing 16 is a distally directed duck bill valve 18 which tapers inward to a sealed configuration, as shown. The diameter of cannula 14 may vary, but typically ranges from 10 to 15 mm for use with the seal assembly 10 of the present invention.

Seal assembly 10 includes a housing 20 which defines an internal passage 22. Housing 20 typically has a substantially cylindrical configuration. A cylindrical guide wall 24 is positioned within passage and is mounted to mounting member 25. Guide wall 24 is fabricated from a rigid plastic material, e.g., ABS, and functions to guide an instrument inserted into passage 22 into alignment with an aperture 26 formed in conical seal member 28 (see FIG. 3). Seal member 28 is fabricated from a resilient material, e.g., polyisoprene or natural rubber, and aperture 26 is adapted to stretch to sealingly engage instruments of varying diameter, e.g., from 4 to 12 mm.

Mounting member 25 is fabricated from a rigid plastic, e.g., lexan, and has a convexly oriented arcuate outer wall 30 that is adapted to cooperate with a concave ring-like track 32 formed on an inner face of housing 20. The arcuate outer wall 30 of mounting member 25 is adapted to rotate within the corresponding ring-like track 32 of housing 20. Although the mounting member 25 is free to rotate around the longitudinal axis A of cannula assembly 12, the rotation of mounting member 25 relative to housing 20 which is of importance to the present invention is the rotation of mounting member 25 relative to the axis transverse to the longitudinal axis A. This rotation may be measured as an angle relative to the longitudinal axis of cannula assembly, as designated by angle "D" in FIG. 2. A lubricant may be provided between outer wall 30 and track 32 to facilitate such rotation. A limiter ring 34 is formed on housing 20 to limit the freedom of movement of mounting member 25 with respect to housing 20. Preferably, limiter ring 34 limits the rotation of mounting member 25 relative to housing 20 to an angular orientation, designated by "D" in FIG. 2, of up to about 25 degrees.

A bellows structure 36 is mounted to and extends distally from mounting member 25. Bellows 36 is fabricated from a resilient material, e.g., polyisoprene, and ensures a substantial fluid-tight seal within housing 20, regardless of the relative position of mounting member with respect to housing 20. A cylindrical protective wall 38 is provided interior of bellows structure 36 to protect bellows 36 from puncture or laceration as an instrument is inserted through housing 20, and to guide such instrument toward duckbill valve 18. As mounting member 25 rotates relative to housing 20, bellows 36 stretches at one side and compresses on the opposite side to accommodate such motion.

Seal assembly 10 may be joined to cannula assembly 12 in a variety of ways. In a preferred embodiment, housing 20 of seal assembly 10 and cannula housing 16 of cannula assembly 12 are adapted to detachably engage each other, e.g., through a bayonnet lock or like mechanical means. Other means of joining seal assembly 10 to cannula assembly 12 will be readily apparent to one of ordinary skill in the art.

Figure 3:
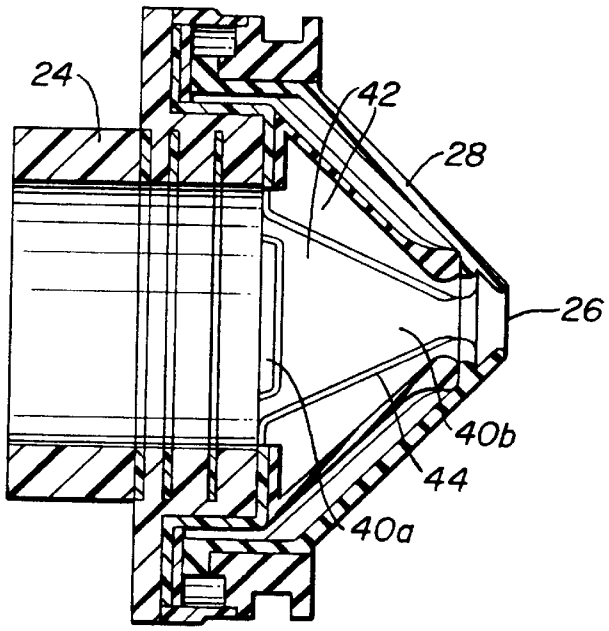
FIG. 3 is a sectional side view of a portion of the seal assembly of the invention.

Referring to FIG. 3, a seal protector 40 may be provided adjacent the proximal side of seal member 28. Seal protector 40 functions to prevent direct contact between the potentially sharp leading edge of a surgical instrument while facilitating the passage of the instrument through aperture 26. A preferred design for seal protector 40 includes a pair of members 40a, 40b having triangularly shaped sections 42 which define slits 44, the respective members 40a, 40b being positioned such that the slits 44 of the first member bisect the triangular sections 42 of the second member, and vice versa. The triangularly shaped sections 42 deflect and contact the seal member 28 as an instrument is passed therethrough, thereby protecting the seal member 28 from puncture/laceration. The seal protectors 40a, 40b described herein are described in more detail in copending, commonly assigned Ser. No. 07/950,205, the contents of which are hereby incorporated by reference.

In use, seal assembly 10 is mounted to cannula assembly 12. An instrument is inserted into seal assembly 10 through passage 22 and into cylindrical guide wall 24 in housing 20. If the axis of the instrument is not perfectly aligned with the axis A of the cannula assembly 12/seal assembly 10, then the surgical instrument will contact the interior of guide wall 24 and/or the wall of seal member 28. This contact causes mounting member 25 to rotate within housing 10, up to the angular limit of limiting ring 34, thereby bringing aperture 26 into alignment with the surgical instrument. The seal protector(s) 40 deflect as the instrument passes through seal member 28. Aperture 26 stretches to accommodate the instrument diameter, as necessary. The instrument passes further distally into the cannula housing 16, passing through duckbill valve 18 and cannula 14, into the body cavity. As the instrument passes distally, mounting member 25 is free to rotate further with respect to housing 20. In particular, if angle D is initially relatively large as the instrument passes through aperture 26, the angle D typically is typically reduced as the instrument passes further into the cannula 14 and/or body cavity. In addition, as the surgeon manipulates the instrument within the body cavity, mounting member 25 is free to rotate relative to housing 20, thereby allowing seal member 28 to maintain sealing engagement with the instrument passed therethrough.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A seal assembly which comprises:

(i) a housing having a passage defining a longitudinal axis and disposed between at least two open ends, (ii) a mounting member rotatably mounted within said housing, and (iii) a seal member at least partially disposed within said passage and mounted to said mounting member, said seal member having an aperture formed therein through which a surgical instrument may pass;

wherein rotation of said mounting member relative to said housing angularly displaces said aperture of said seal member relative to said longitudinal axis.

2. The seal assembly of claim 1, further comprising at least one guide wall at least partially disposed within said housing, adjacent said seal member, wherein said guide wall aids in guiding said surgical instrument through said seal member.

3. A seal assembly of claim 1, further comprising a limiting ring disposed within said housing for limiting the rotation of said mounting member with respect to said housing.

4. The seal assembly of claim 1, wherein said mounting member includes a convex, arcuate outer face in sliding contact with an internal concave ring-like track disposed within said housing.

5. The seal assembly of claim 1, further comprising at least one seal protect or disposed within said housing and positioned adjacent said seal member for preventing direct contact of a leading edge of said surgical instrument with said seal member.

6. The seal assembly of claim 1, wherein said housing defines a longitudinal axis and said mounting member is adapted to rotate up to about 25 degrees with respect to said longitudinal axis.

7. The seal assembly of claim 1, wherein said housing further includes a bellows structure extending from said mounting member, said bellows structure ensuring a substantially fluid-tight seal within said housing, regardless of the relative position of said mounting member with respect to said housing.

8. The seal assembly of claim 1, wherein said housing is adapted to be detachably mounted at one end to a cannula assembly for providing a substantially fluid-tight seal when said instrument is inserted into said seal assembly and through said cannula assembly.

9. The seal assembly of claim 1, wherein said seal member is adapted to accommodate instruments ranging in diameter from 4 to 15 mm.

10. The seal assembly of claim 1, wherein said seal member is conical and is fabricated from a resilient material.

11. In combination:

(a) a cannula assembly which includes a cannula housing mounted at one end to a cannula, said cannula housing including a valve assembly disposed at least partially within said housing, said valve assembly being adapted to provide a fluid-tight seal; and (b) a seal assembly removably mounted with respect to said cannula assembly, said seal assembly including a seal assembly housing including mounting means for mounting to said cannula housing and having a passage defining a longitudinal axis and disposed between at least two open ends, a mounting member rotatably mounted within said seal assembly housing, and a seal member at least partially disposed within said passage and mounted to said mounting member, said seal member having an aperture formed therein through which a surgical instrument may pass;

wherein rotation of said mounting member relative to said seal assembly housing angularly displaces said aperture of said seal member with respect to the longitudinal axis.

12. The combination of claim 11, wherein said seal assembly is detachably mounted to said cannula assembly.

*13. A seal assembly which comprises:*

*(i) a housing having a passage defining a longitudinal axis and disposed between at least two open ends;*

*(ii) a mounting member movably mounted within said housing;*

*(iii) a seal member at least partially disposed within said passage and mounted to said mounting member, said seal member having an aperture formed therein through which a surgical instrument may pass; and*

*(iv) a bellows structure extending from said mounting member and secured to said housing, said bellows structure ensuring a substantially fluid-tight seal between said mounting member and said housing, regardless of the relative position of said mounting member with respect to said housing;*

*wherein movement of said mounting member relative to said housing displaces said aperture of said seal member relative to said longitudinal axis.*

*14. A seal assembly according to claim 13, wherein said mounting member is rotatably mounted within said housing.*

*15. A seal assembly according to claim 13, wherein said bellows structure defines a first side and a second side which is opposite to said first side, and wherein movement of said mounting member relative to said housing causes said first side of said bellows structure to stretch and said opposite side of said bellows structure to compress.*

*16. A seal assembly according to claim 13, wherein said bellows structure is fabricated from a resilient material.*

*17. A seal assembly according to claim 16, wherein said resilient material is polyisoprene.*

*18. In combination:*

*(a) a cannula assembly which includes a cannula housing mounted at one end to a cannula, said cannula housing including a valve assembly disposed at least partially within said housing, said valve assembly being adapted to provide a fluid-tight seal;*

*(b) a seal assembly removably mounted with respect to said cannula assembly, said seal assembly including a seal assembly housing including mounting means for mounting to said cannula housing and having a passage defining a longitudinal axis and disposed between at least two open ends, a mounting member movably mounted within said seal assembly housing, and a seal member at least partially disposed within said passage and mounted to said mounting member, said seal member having an aperture formed therein through which a surgical instrument may pass; and*

*(c) a bellows structure extending from said mounting member and secured to said seal assembly housing, said bellows structure ensuring a substantially fluid-tight seal between said mounting member and said seal assembly housing, regardless of the relative position of said mounting member with respect to said seal assembly housing;*

*wherein movement of said mounting member relative to said seal assembly housing displaces said aperture of said seal member with respect to the longitudinal axis.*

*19. A combination according to claim 18, wherein said mounting member is rotatably mounted within said housing.*

* * * * *